US00PP21510P3

(12) United States Plant Patent
Delbard

(10) Patent No.: US PP21,510 P3
(45) Date of Patent: Nov. 23, 2010

(54) HYBRID TEA ROSE PLANT NAMED 'DELGRAMAU'

(50) Latin Name: *Rosa hybrida*
Varietal Denomination: Delgramau

(75) Inventor: Arnaud Delbard, Commentry (FR)

(73) Assignee: Pépinières et Roseraies Georges Delbard, Malicorne (FR)

( * ) Notice: Subject to any disclaimer, the term of this patent is extended or adjusted under 35 U.S.C. 154(b) by 0 days.

(21) Appl. No.: 12/453,139

(22) Filed: Apr. 30, 2009

(65) Prior Publication Data

US 2010/0162445 P1 Jun. 24, 2010

(30) Foreign Application Priority Data

Dec. 18, 2008 (EM) ..... 2008/2522

(51) Int. Cl.
*A01H 5/00* (2006.01)

(52) U.S. Cl. ..... Plt./130

(58) Field of Classification Search ..... Plt./130
See application file for complete search history.

*Primary Examiner*—Kent L Bell
(74) *Attorney, Agent, or Firm*—Buchanan Ingersoll & Rooney PC

(57) ABSTRACT

A new and distinct variety of Hybrid Tea rose plant is provided which abundantly forms on a substantially continuous basis attractive long-lasting double lilac-colored flowers that bear a strong fragrance. The petals commonly detach cleanly without drying on the plant. The new variety was created by artificial pollination at Hyères, France. The growth habit is bushy. The vegetation is vigorous and good disease resistance to Blackspot and Powdery Mildew has been observed during observation to date. The new plant is well suited for growing as attractive ornamentation in the landscape.

1 Drawing Sheet

Figures 1, 2, 3, 4, 5, 6, 7, 8, 9, 10, 11, 12, 13, 14, 15, 16:
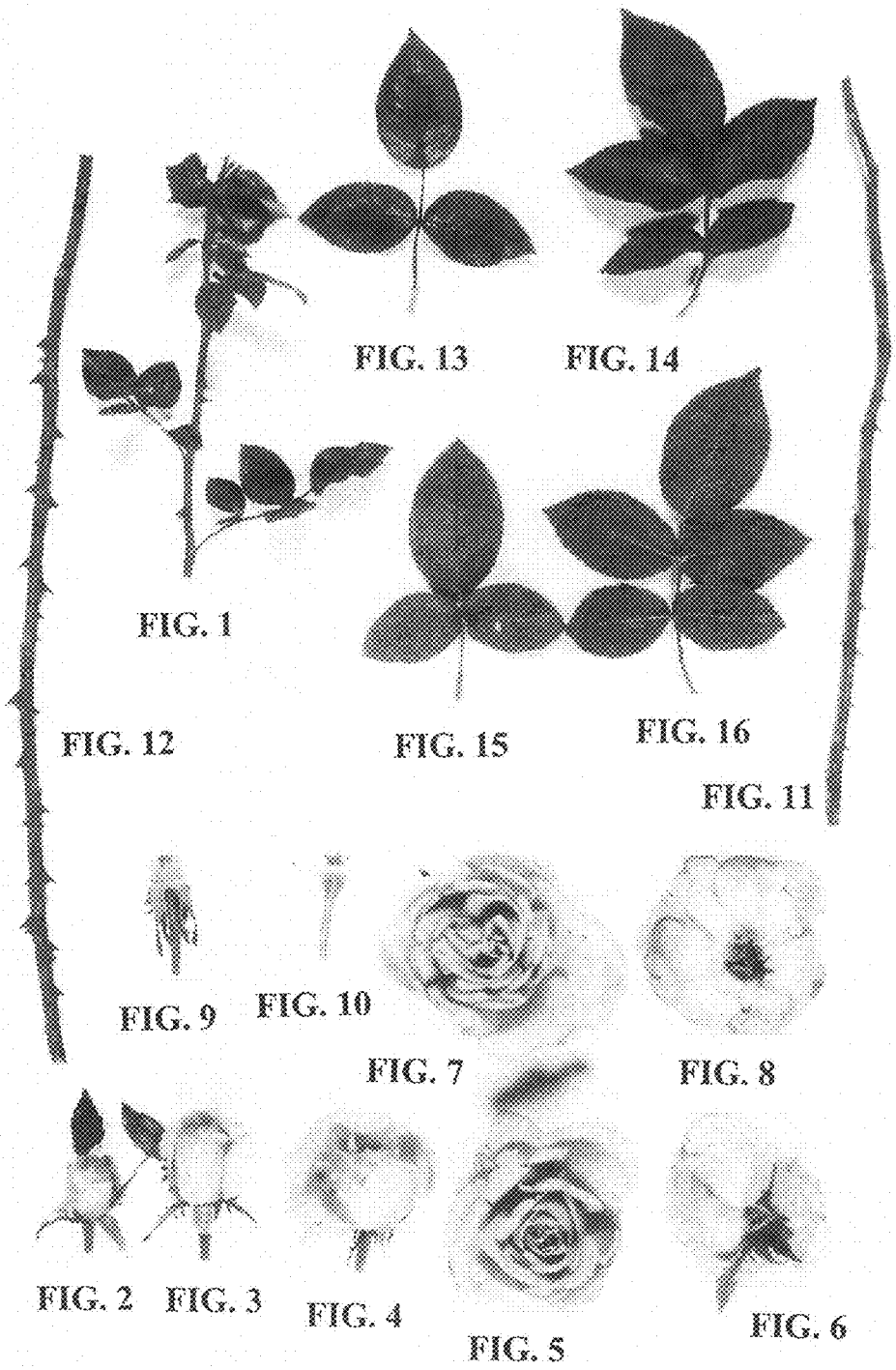

Botanical/commercial classification: *Rosa hybrida*/Hybrid Tea Rose Plant.

Varietal denomination: cv. Delgramau.

SUMMARY OF THE INVENTION

The new *Rosa hybrida* Hybrid Tea rose plant was created by artificial pollination carried out during 1998 in a greenhouse at Hyères, France, wherein two parents were crossed which previously had been studied in the hope that they would contribute the desired characteristics. The female parent (i.e., the seed parent) was the 'Delge' variety (non-patented in the United States). The male parent (i.e., the pollen parent) was the 'Adharman' variety (non-patented in the United States). The 'Delge' variety sometimes is identified as CENTENAIRE DE LOURDES. The 'Adharman' variety sometimes is identified as COMMANDANT COUSTEAU.

The parentage of the new plant can be summarized as follows:

'Delge'×'Adharman'.

The seeds resulting from the above pollination were sown and small plants were obtained which were physically and biologically different from each other. Selective study resulted in the identification of a single plant of the new variety.

It was found through careful study that the new variety of Hybrid Tea rose plant of the present invention exhibits the following combination of characteristics:

(a) from a physical point of view forms green mature wood, displays a bushy growth habit with glossy foliage, and forms attractive long-lasting double lilac-colored flowers that bear a strong fragrance, and (b) from the biological point of view forms vigorous vegetation, produces flowers in abundance on a substantially continuous basis, and exhibits good resistance to Blackspot and Powdery Mildew.

The new variety well meets the needs of the horticultural industry and is particularly well suited for growing outdoors as attractive ornamentation. A bush or climbing growth habit is displayed.

The new variety can be readily distinguished from its ancestors in view of the combination of characteristics described herein. For instance, the new variety can be readily distinguished from its 'Delge' variety parent through an examination of blossoms and overall plant vigor. More specifically, the blossoms of the new variety are larger and possess a greater number of petals than the 'Delge' variety. Also, the new variety displays more vigorous vegetation than the 'Delge' variety. Unlike the new variety, the 'Adharman' variety forms dark red blossoms.

The new variety of the present invention also can be readily distinguished from the 'Delgrarose' variety (U.S. Plant patent application Ser. No. 12/453,138, filed concurrently herewith) which was the product of the same cross pollination. The blossoms of the 'Delgrarose' variety possess a greater number of petals and are pink in coloration rather than the lilac coloration displayed by the present variety.

The new variety has been found to undergo asexual propagation and can be readily reproduced by conventional routes, such as budding (i.e., eye grafting). This asexual reproduction as performed at Malicorne, France, has demonstrated that the characteristics of the new variety are stable and are strictly transmissible from one generation to another. Accordingly, the new variety can be asexually reproduced in a true-to-type manner.

The new variety has been named 'Delgramau'.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown outdoors in central France, at Malicorne, France.

FIG. 1—illustrates a specimen of a young shoot;

FIG. 2—illustrates a specimen of a floral bud at the opening of the sepals;

FIG. 3—illustrates a specimen of a floral bud at the opening of the petals;

FIG. 4—illustrates specimens of a flower in the course of opening;

FIG. 5—illustrates a specimen of an open flower—plan view—obverse;

FIG. 6—illustrates a specimen of an open flower—plan view—reverse;

FIG. 7—illustrates a specimen of a fully open flower—plan view—obverse;

FIG. 8—illustrates a specimen of a fully open flower—plan view—reverse;

FIG. 9—illustrates a specimen of a floral receptacle showing the arrangement of the stamens and pistils;

FIG. 10—illustrates a specimen of a floral receptacle showing the arrangement of the pistils (stamens and sepals removed);

FIG. 11—illustrates a specimen of a flowering stem;

FIG. 12—illustrates a specimen of a main branch;

FIG. 13—illustrates a specimen of a leaf with three leaflets—plan view—upper surface;

FIG. 14—illustrates a specimen of a leaf with five leaflets—plan view—upper surface;

FIG. 15—illustrates a specimen of a leaf with three leaflets—plan view—under surface; and FIG. 16—illustrates a specimen of a leaf with five leaflets—plan view—under surface.

DETAILED DESCRIPTION

The chart used in the identification of the colors is that of The Royal Horticultural Society (R.H.S. Colour Chart-2001). The description is based on the observation of plants grafted on *Rosa laxa* understock while growing outdoors in central France, at Malicorne, France.

Class: Hybrid Tea.

Plant:

*Height.*—Plants which were pruned to a height of 20 to 30 cm produce floral stems having an average height of approximately 70 to 150 cm, and an average stem length of approximately 90 cm.

*Width.*—Approximately 50 to 60 cm on average.

*Habit.*—Bushy.

Branches:

*Color.*—Young shoots: when approximately 20 cm long, exhibit green coloration, Yellow-Green Group 146A. Floral stems: Green Group 137B. Mature wood: Green Group 137B and Purple Group 79A.

*Diameter.*—Commonly approximately 10 to 18 mm (average 12 mm).

*Thorns.*—Configuration: convex on the upper edge and concave on the under edge. Quantity, length and frequency: on a typical floral stem having a length of 90 cm, there commonly are no thorns on the 30 cm below the bud, for the next 30 cm no or very few thorns, and for the last 30 cm some thorns irregularly arranged having lengths of approximately 3 mm to 1 cm and an average length of approximately 8 mm. On a young shoot having a length of approximately 30 cm, there commonly are few thorns. Color: on floral stems the coloration of the thorns is Greyed-Purple Group 184A to Red-Purple Group 60B, and on mature wood the thorns are Greyed-Purple Group 184A to Red-Purple Group 60B.

*Leaves.*—Number: typical for the class and commonly number approximately 90 to 100. Size: terminal leaflets commonly are approximately 60 to 90 mm (average 70 mm) in length and approximately 40 to 65 mm (average 46 mm) in width. Stipules: adnate, medium in size, and commonly 20 to 30 mm (average 25 mm) in length, approximately 5 to 8 mm (average 7 mm) in width at the mid-point, and approximately 13 to 20 mm (average 15 mm) at the distal end.

*Leaflets.*—Number: commonly 3 and 5. Shape: general obovate, with an acuminate apex, rounded at the base, and convex in cross section. Serration: present, single, and irregular. General appearance: consistent with strong glossiness. Petiole: commonly bears some prickles (often 1 to 3 per petiole), and the inner surface is grooved with non-glandular edges. Petiole color on floral stems: Greyed-Purple Group 183C. Petiole color on mature wood: Yellow-Green Group 146A on the upper surface and Yellow-Green Group 146C on the under surface. Petiole length of terminal leaflet: approximately 16 to 24 mm, approximately 20 mm on average, with a standard deviation of 0.22 mm. Petiole diameter: approximately 2 mm. Rachis color: Yellow-Green Group 144A. Rachis Length: approximately 5.5 cm. Rachis diameter: approximately 1 to 2 cm. Rachis texture: generally smooth. Terminal leaflet length: approximately 60 to 90 mm, approximately 70 mm on average, with a standard deviation of 0.67 mm. Terminal leaflet width: approximately 40 to 65 mm, approximately 55 mm on average, with a standard deviation of 0.41 mm. Leaflet color of young shoot: Yellow-Green Group 147A with some coloration of Greyed-Orange Group 175A on the upper and under surfaces. Leaflet color on floral stem: Yellow-Green Group 147A on the upper surface and Yellow-Green Group 146C on the under surface. Leaflet color of mature wood: Yellow-Green Group 147A on the upper surface, and Yellow-Green Group 146C on the under surface. Venation: in a typical alternately arranged pattern, and the coloration commonly is Yellow-Green Group 151A on mature wood, and Greyed-Purple Group 183C on the extremities of young stems and floral stems.

Inflorescence:

*Number of flowers.*—Generally one to three per stem.

*Peduncle.*—Erect, stiff, Yellow-Green Group 144B in coloration with some Greyed-Purple Group 183C, and approximately 85 to 115 mm in length (average approximately 100 mm), and approximately 7 mm in diameter.

*Sepals.*—Number 5. Configuration: elongated, sharply pointed, one or two sepals commonly possess no extensions, and two or three sepals commonly possess medium extensions. The extensions are denticulate. The sepal length commonly is approximately 3.5 cm, and the sepal width commonly is approximately 1.1 cm. Color: Yellow-Green Group 143B on the upper surface and Yellow-Green Group 138B on the under surface.

*Buds.*—Shape: ovate in longitudinal section just before the opening of the sepals. Size before calyx breaks: the bud lengths are approximately 25 to 35 mm, with an average length of approximately 30 mm, and the bud diameters commonly are approximately 35 mm just before the opening of the petals. Color as calyx breaks: Red Group 53B. Size after calyx breaks: the bud lengths are approximately 35 to 40 mm, with an average length of approximately 37 mm. Color after calyx breaks: inside: Red Group 54A.

*Flower.*—Time: when growing outdoors flowering commonly begins early at central France, i.e., commonly by the end of May. Shape: rounded when viewed from above. Form: double, flattened at the upper part when viewed from the side, and flattened convex to convex at the lower part when viewed from the side. Diameter: medium, approximately 9 to 13 cm, and approximately 11 cm on average, with a standard deviation of 0.5 cm. Petal number: commonly approximately 28 to 40, and an average of approximately 35. Petal size (second row from outside): the length is approximately 50 to 64 mm with a mean of approximately 57 mm, and a standard deviation of 4 mm; and the width is approximately 55 to 70 mm with a mean of approximately 64 mm, and a standard deviation of 6 mm. Petal shape: the overall shape is generally rounded, the undulation of the petal margins is weak, and the reflexing of the margins is very weak. The petal apex tends to be relatively flat and the petal base tends to the flattened-convex in configuration. Petal color: the following description of a nearly fully open flower was made outdoors at the end of summer. Petal color (middle zone): on the inner surface Purple Group 75C, and on the outer surface Purple Group 75C. Petal color (marginal zone): on the inner surface Purple Group 75C, and on the outer surface Purple Group 75C. Petal spot at base: small in size, and commonly covers only approximately 3 percent of petal surface. Color of spot inner side: Yellow Group 7D. Color of spot outer side: Yellow Group 7D. Stamens: approximately 150 in number and are somewhat regularly arranged. Filaments: medium in length, not all possess an anther, and when the flower is partially open Yellow-Orange Group 14A in coloration. Anthers: medium in size, all open at approximately the same time, and the immature coloration is Yellow-Orange Group 14A. Pollen: sparse in quantity and Yellow-Orange Group 21A in coloration. Pistils: approximately 90 in number. Styles: medium in length and Red Group 43C in coloration. Stigmas: Yellow-Orange Group 18B, and generally are present at the same level as the anthers. Hips: in longitudinal section they are in the shape of a funnel and commonly are approximately 23 to 28 mm in diameter on average. Seeds: present. Lastingness: the blossoms commonly last approximately 6 days on the plant under normal environmental conditions and approximately 4 days when cut and placed in a vase. Petal drop: the petals commonly detach cleanly without drying on the plant. Fragrance: strong, and commonly citrus-like, similar to that of grapefruit.

Development:

*Vegetation.*—Vigorous.

*Blooming.*—Very abundant and substantially continuous.

*Resistance to diseases.*—Excellent, particularly with respect to Blackspot and Powdery Mildew.

*Winter hardiness.*—Good under observations to date.

*Drought tolerance.*—Good under observations to date.

I claim:

1. A new and distinct Hybrid Tea Rose plant that exhibits the following combination of characteristics:

(a) from a physical point of view forms green mature wood, displays a bushy growth habit with glossy foliage, and forms attractive long-lasting double lilac-colored flowers that bear strong fragrance, and (b) from a biological point of view forms vigorous vegetation, produces flowers in abundance on a substantially continuous basis, and exhibits good resistance to Blackspot and Powdery Mildew;

substantially as illustrated and described.

* * * * *